United States Patent
Linker

(10) Patent No.: US 8,897,863 B2
(45) Date of Patent: Nov. 25, 2014

(54) ARRHYTHMIA DETECTION USING HIDDEN REGULARITY TO IMPROVE SPECIFICITY

(71) Applicant: University of Washington through its Center for Commercialization, Seattle, WA (US)

(72) Inventor: David Thor Linker, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

(21) Appl. No.: 13/886,240

(22) Filed: May 2, 2013

(65) Prior Publication Data

US 2013/0296680 A1 Nov. 7, 2013

Related U.S. Application Data

(60) Provisional application No. 61/642,268, filed on May 3, 2012.

(51) Int. Cl.
| | | |
|---|---|---|
| *A61B 5/02* | (2006.01) | |
| *A61B 5/04* | (2006.01) | |
| *A61B 5/00* | (2006.01) | |
| *A61B 5/046* | (2006.01) | |

(52) U.S. Cl.
CPC ........... *A61B 5/04012* (2013.01); *A61B 5/7221* (2013.01); *A61B 5/046* (2013.01)
USPC ............ 600/515; 600/508; 600/509; 600/516

(58) Field of Classification Search
USPC ................................. 600/508–509, 515–516
See application file for complete search history.

(56) References Cited

U.S. PATENT DOCUMENTS

| | | |
|---|---|---|
| 4,248,244 A | 2/1981 | Charnitski |
| 5,348,008 A | 9/1994 | Bomn |
| 6,487,442 B1 | 11/2002 | Wood |
| 6,701,183 B2 | 3/2004 | Baker |
| 6,705,998 B2 | 3/2004 | Stergiopoulos |
| 7,094,207 B1 | 8/2006 | Koh |
| 7,630,756 B2 | 12/2009 | Linker |
| 8,326,407 B2 | 12/2012 | Linker |

(Continued)

FOREIGN PATENT DOCUMENTS

| | | |
|---|---|---|
| EP | 1 219 237 A2 | 7/2002 |
| WO | 02/056961 A2 | 7/2002 |
| WO | 03/105020 A2 | 12/2003 |

OTHER PUBLICATIONS

Goldberger, A.L., et al., PhysioBank, PhysioToolkit, and PhysioNet: Components of a New Research Resource for Complex Physiologic Signals, Circulation 101(23):e215-e220, Jun. 2000.

(Continued)

*Primary Examiner* — Nicole F Lavert
(74) *Attorney, Agent, or Firm* — Christensen O'Connor Johnson Kindness PLLC

(57) ABSTRACT

A method for identifying a target arrhythmia, for example, atrial fibrillation, with very high specificity includes obtaining heart rhythm data such as EKG data, selecting and analyzing a segment of the data for arrhythmia, if an arrhythmia is found then reanalyzing the segment of data for a hidden regularity that would indicate the data is not the target arrhythmia. If no hidden regularity is found, then identifying the segment as the target arrhythmia.

19 Claims, 6 Drawing Sheets

(56) References Cited

U.S. PATENT DOCUMENTS

| | | | |
|---|---|---|---|
| 2002/0052557 | A1 | 5/2002 | Griffin |
| 2002/0147409 | A1 | 10/2002 | Baker |
| 2002/0151806 | A1 | 10/2002 | Starobin |
| 2003/0130586 | A1 | 7/2003 | Starobin |
| 2006/0089559 | A1 | 4/2006 | Barbieri |
| 2006/0167361 | A1 | 7/2006 | Bennett |
| 2007/0179390 | A1 | 8/2007 | Schecter |
| 2010/0241017 | A1* | 9/2010 | Johnson et al. ............... 600/509 |

OTHER PUBLICATIONS

Jager, F., et al, "Long-Term ST Database: A Reference for the Development and Evaluation of Automated Ischaemia Detectors and for the Study of the Dynamics of Myocardial Ischaemia," Medical & Biological Engineering & Computing 41(2):172-182, 2003.

Moody, G.B., et al., "A New Method for Detecting Atrial Fibrillation Using R-R Intervals," Computers in Cardiology 10:227-230, 1983.

Petrutiu, S., et al., "Abrupt Changes in Fibrillatory Wave Characteristics at the Termination of Paroxysmal Atrial Fibrillation in Humans," Europace 9:466-470, 2007.

Stein, P.K., et al., "Clinical and Demographic Determinants of Heart Rate Variability in Patients Post Myocardial Infarction: Insights From the Cardiac Arrhythmia Suppression Trial (CAST)," Clinical Cardiology 23(3):187-94, Mar. 2000.

Ang, N.H., "Real Time Electrocardiogram Signal Processing for Atrial Fibrillation Detection," Final Report of the Postgraduate Programme: Mathematics for Industry, Stan Ackermans Institute, Eindhoven University of Technology, Netherlands, Jan. 2004, 53 pages.

Bassingthwaighte, J.B., and G.M. Raymond, "Evaluation of the Dispersional Analysis Method for Fractal Time Series," Annals of Biomedical Engineering 23(4):491-505, Jul.-Aug. 1995.

"CardioNet—Monitoring at the Speed of Life: How It Works," © 2002 CardioNet, <http://www.cardionet/how.html> [retrieved Jan. 26, 2006], 1 page.

Duverney, D., et al., "High Accuracy of Automatic Detection of Atrial Fibrillation Using Wavelet Transform of Heart Rate Intervals," Pacing and Clinical Electrophysiology 25(4, Part 1):457-462, Apr. 2002.

"Geratherm Awarded Licence for Cardio Monitor," Geratherm Medical AG, Geschwenda, Germany, May 26, 2004, <http://www.geratherm.com/en/iv_pressemitteilungen> [retrieved Jan. 26, 2006], 4 pages.

"Instromedix—Cardiac Event Recorders & Pacemaker Checks," Instromedix, A Card Company, © 2004 Card Guard® Group of Companies, <http://www.instromedix.com> [retrieved Jan. 26, 2006], 1 page.

Israel, C.W., et al., "Long-Term Risk of Recurrent Atrial Fibrillation as Documented by an Implantable Monitoring Device: Implications for Optimal Patient Care," Journal of the American College of Cardiology 43(1):47-52, Jan. 2004.

Malik, M., "Heart Rate Variability: Standards of Measurement, Physiological Interpretation, and Clinical Use," European Heart Journal 17(3):354-381, Mar. 1996.

Page, R.L., et al., "Asymptomatic or 'Silent' Atrial Fibrillation: Frequency in Untreated Patients and Patients Receiving Azimilide," Circulation 107(8):1141-1145, Mar. 2003.

Swerdlow, C.D., et al., "Detection of Atrial Fibrillation and Flutter by a Dual Chamber Implantable Cardioverter-Defibrillator," Circulation 101(8):878-885, Feb. 2000.

Tateno, K., and L. Glass, "Automatic Detection of Atrial Fibrillation Using the Coefficient of Variation and Density Histograms of RR and ΔRR Intervals," Medical and Biological Engineering and Computing 39(6):664-671, Nov. 2001.

Wolk, R., et al., "The Incidence of Asymptomatic Paroxysmal Atrial Fibrillation in Patients Treated With Propranolol or Propafenone," International Journal of Cardiology 54(3):207-211, Jun. 1996.

European Search Report mailed Sep. 28, 2009, issued in corresponding European Patent Application No. EP 05 809 951.6, filed Oct. 19, 2005, 2 pages.

European Examination Report mailed Jan. 13, 2010, issued in corresponding European Patent Application No. EP 05 809 951.6, filed Oct. 19, 2005, 11 pages.

International Search Report and Written Opinion mailed Jan. 20, 2010, issued in corresponding International Application No. PCT/US2009/044957, filed May 22, 2009, 6 pages.

Office Action mailed Jun. 25, 2013, from U.S. Appl. No. 13/670,246, filed Nov. 6, 2012, 10 pages.

\* cited by examiner

ARRHYTHMIA DETECTION USING HIDDEN REGULARITY TO IMPROVE SPECIFICITY

CROSS-REFERENCE TO RELATED APPLICATION

This application claims the benefit of Provisional Application No. 61/642,268, filed May 3, 2012, the entire disclosures of which are hereby incorporated by reference herein.

STATEMENT OF GOVERNMENT LICENSE RIGHTS

This invention was made with Government support under 1 R 41 HL090106-1A1, awarded by the National Institutes of Health (NIH). The U.S. Government has certain rights in the invention.

BACKGROUND

Various types of heart rhythm disorders are known, some of which are life-threatening and require immediate attention and treatment, such as ventricular fibrillation. Other arrhythmias may require treatment, and/or may be symptomatic of other underlying conditions requiring treatment, but are typically not immediately life-threatening. Atrial fibrillation ("AF"), for example, is a relatively common cardiac arrhythmia associated with increased risk of stroke and death. Other less-common cardiac arrhythmias that would be beneficial to diagnose include, but are not limited to, paroxysmal ventricular tachycardia, paroxysmal atria tachycardia, supraventricular tachycardia, and sinus tachycardia. Although the following disclosure will, for simplicity, refer to AF, it will be understood that the disclosed methods are also generally applicable to other less-common cardiac arrhythmias.

AF is the most common disturbance of the heart rhythm requiring treatment. Epidemiologic data estimates that 2.2 million individuals suffer from AF in the United States. The prevalence of AF is approximately 2-3% in patients older than 40 years of age and 6% in those individuals over 65 years and 9% in individuals over 80 years old. As the U.S. population ages, AF will become more prevalent. It is estimated that over 5 million Americans will suffer from AF by the year 2050. AF is associated with a doubling of mortality rate of people afflicted with AF compared to people who are not, and an increased risk of stroke of about 5% per year.

AF can be either symptomatic or asymptomatic, and can be paroxysmal or persistent. Symptomatic AF is a medical condition wherein symptoms are readily detectable by experts in the field. AF is usually diagnosed when a patient exhibits associated symptoms or complications, such as palpations, congestive heart failure or stroke. AF may also be diagnosed incidentally during a routine medical evaluation.

Patients with asymptomatic paroxysmal AF may be exposed to the risk of devastating consequences such as stroke, congestive heart failure, or tachycardia-mediated cardiomyopathy, for years before a definitive diagnosis of AF can be made.

Current standard techniques and devices for detecting AF include a resting electrocardiogram, which records about 15 seconds of cardiac activity, a Holter monitor, which records 24-48 hours of cardiac activity during routine daily activities, and an event monitor, which only records cardiac activity when the patient activates the monitor because the patient has detected symptoms associated with AF. These diagnostic methods and tools have significant limitations in diagnosing AF and assessing the efficacy of treatment because of the limited recording time windows of these methods and tools.

Moreover, pharmacologic treatment of AF may convert patients with symptomatic AF into patients with asymptomatic AF. In a retrospective study of four studies comparing the drug Azimilide to a placebo where, in the absence of symptoms, routine trans-telephonic electrocardiograms were recorded for 30 seconds every two weeks, asymptomatic AF was present in 17% of the patients. In another study of 110 patients with permanently implanted pacemakers who had a history of AF, the condition was diagnosed in 46% of the patients using electrocardiogram recording and in 88% of the patients using stored electrograms recorded by the implanted pacemaker.

Review of data stored in implanted devices, such as pacemakers, revealed that 38% of AF recurrences lasting greater than 48 hours were completely asymptomatic. Finally, using data obtained from ambulatory monitors used on patients with paroxysmal AF over a 24-hour period, studies show a high frequency of occurrence of asymptomatic AF among patients treated with the drugs propranolol or propafenone. In the above-mentioned study, 22% of the patients on propranolol and 27% of the patients on propafenone were diagnosed with asymptomatic AF.

Under-detection and under-recognition of AF in patients may have significant clinical consequences, including clinical exposure of patients to an increased risk of cardio-embolic stroke before detection of the arrhythmia and initiation of appropriate stroke prevention measures, difficulty of assessment of the efficacy of rhythm control intervention, and overestimation of successful maintenance of sinus rhythm.

However, screening for many dangerous arrhythmias can be problematic. A known challenge in the detection of dangerous arrhythmias from heart activity data such as EKG data is that a generally healthy heart may often exhibit some variability in the EKG data that can confuse or mislead automated detection algorithms. Relatively benign variability may include premature atrial contraction, premature ventricular contraction, and normal sinus arrhythmia.

A common problem with screening for potentially dangerous heart rhythm irregularities, such as atrial fibrillation, ventricular tachycardia, and the like, is that existing detection methods lack sufficient specificity. Existing detection methods produce a significant number of false positives, generating anxiety in healthy subjects, causing expensive technician review, and possibly spurring unnecessary, expensive, potentially uncomfortable, and inconvenient additional testing.

Detection of AF, automatically or manually, based on statistical data, requires the use of thresholds defined with respect to sensitivity and specificity. The thresholds used define the point beyond which a set of data indicates existence of AF. Sensitivity and specificity are defined as follows. In a dichotomous experiment, a given event, e, falls into one of two sets, such as a set of positive events, P, and a set of negative events, N. The set P includes events p and the set N includes events n.

A detection test may be performed to determine that the given event e belongs to the set P or to the set N in a dichotomous experiment. Sensitivity is a measure of how well the detection test can correctly identify the given event e of the set P as belonging to the set P. Such events e that are correctly identified as belonging to the set P are known as true positives ("TP"). Such events e that are misidentified as belonging to the set N are known as false negatives ("FN").

Sensitivity is defined as the ratio of the number of true positive events detected correctly by the test to the total number of actual positive events p. The total number of actual positive events is equal to the sum of the TP and FN. That is, sensitivity=TP/(TP+FN). A low sensitivity detection test will misidentify more positive events as belonging to the set N than a high sensitivity detection test.

Specificity is the dual of sensitivity and is a measure of how well the detection test can correctly identify the given event e of the set N as belonging to the set N. Such events e that are correctly identified as belonging to the set N are known as true negatives ("TN"). Such events e that are misidentified as belonging to the set P are known as false positives ("FP"). Specificity is defined as the ratio of the number of true negative events detected correctly by the test to the total number of actual negative events n. The total number of actual negative events is equal to the sum of the TN and FP. That is, specificity=TN/(TN+FP). A low specificity detection test will misidentify more negative events as belonging to the set P than a high specificity detection test.

A prominent characteristic of AF is heart rate variability. There have been attempts to use the variability of heart interbeat ("RR") intervals directly to identify AF, resulting in a sensitivity of 94% and specificity of 97% using a threshold based on the Kolmogorov-Smirnov test. The Kolmogorov-Smirnov test is used to decide if a statistical sample belongs to a population with a specific probability distribution.

Long-term monitoring of cardiac activity is desirable for timely detection of AF, but the storage requirements can be prohibitive. To digitize a single channel EKG at 100 samples per second and 10-bit resolution, which constitute near minimum requirements for a high quality signal, for 90 days of continuous recording requires 927 megabytes of storage. Although providing this amount of storage is possible, it is also costly. Advances in electronics allow the design of portable devices that can pre-process and classify the signals to avoid storage of normal rhythms and save the storage capacity for recording of abnormal rhythms, for example, rhythms indicating episodes of atrial fibrillation.

A device is desired for the long-term monitoring of a subjects heart rhythm that is inexpensive, non-invasive, highly accurate, and convenient for the patient. These requirements at least indicate that the monitoring device should be light and small. As such, a device is desired with low power requirements and with a significant amount of storage. The storage capacity may possibly be extended by using an algorithm for the elimination of EKG data that indicate very low-probability of AF or other target arrhythmia. This algorithm should be small in size and simple in operation to reduce processing power needs and electrical power requirements.

For response to and treatment of ventricular tachycardia and ventricular fibrillation in real-time, often an implantable cardiac defibrillator ("ICD") is surgically implanted in the patient and coupled with the heart to monitor heart rhythm and detect these life-threatening rhythm disturbances. The ICD typically includes logic components implemented in software/firmware and/or hardware for detecting arrhythmia. Once life-threatening arrhythmia is detected, the ICD logic component may, based on a discrimination algorithm, determine that some action, such as administering an electric shock (defibrillation), must be taken to treat the arrhythmia.

However, this determination can be erroneous. In some ICDs such inappropriate shocks can occur in 15% of all patients within a 46-month follow-up. Certain sub-populations may have a higher rate of inappropriate shocks, for example, this can occur in as many as 38% of younger patients. A common cause of inappropriate shock in these patients is AF, although virtually any supraventricular tachycardia can cause an inappropriate shock.

When not needed, an electric shock causes extreme discomfort and/or pain to the patient and may be potentially dangerous. Accordingly, a more accurate discrimination algorithm is needed to discriminate between cases where an electric shock is needed and cases where an electric shock is not needed. One approach that has been used is based on the heart rate, or beat-to-beat intervals. Another approach uses the morphology of the electrocardiographic complexes to help discriminate, with a representative recent method being the use of wavelet-transforms. In spite of these methods, inappropriate shocks continue to be a problem in such devices.

SUMMARY

This summary is provided to introduce a selection of concepts in a simplified form that are further described below in the Detailed Description. This summary is not intended to identify key features of the claimed subject matter, nor is it intended to be used as an aid in limiting the scope of the claimed subject matter.

It is desirable to detect particular target arrhythmias with high specificity, in order to prevent false positives, and all of the personal anxieties and costs associated with such false positives. A high specificity method for detecting a target arrhythmia, for example, atrial fibrillation, in heart rhythm data generated by monitoring the electrical activity of a heart, is disclosed. The activity of the heart can be monitored in a plurality of ways without affecting the methods disclosed, including but not limited to electrical activity, pulse oximetry, or phonocardiography. Currently, the most frequently used mode for monitoring a heart is to monitor the electrical activity of the heart. The heart rhythm data is analyzed in segments, i.e. analysis segments, containing a predetermined number of contiguous heart beat intervals. The analysis segment is analyzed to identify an irregularity in the interval data indicating an arrhythmia, wherein the arrhythmia may not be the target arrhythmia. If an arrhythmia is indicated, then the analysis segment is reanalyzed to identify a hidden regularity that would indicate the arrhythmia is not the target arrhythmia. If a hidden regularity is not found in the analysis segment, then the analysis segment is designated as the target arrhythmia, and is stored with the designation on a computer readable medium.

In an embodiment the heart rhythm data is electrocardiograph data obtained from a wearable monitor device having an electrode, a power supply, a microprocessor, a data storage device, and/or a QRS detector.

In an embodiment the segments contain less than twenty-two heart beat intervals.

In an embodiment the step of reanalyzing the analysis segment comprises calculating a combinatorial property or value of the interval data in the analysis segment, and comparing that combinatorial property with a threshold value to determine if a hidden regularity is present. In an embodiment the threshold value is determined by (i) analyzing a database of heart rhythm data for which the arrhythmia properties of the heart rhythm data is known; (ii) calculating an inaccuracy rate associated with comparing the calculated combinatorial property with a range of threshold values; and (iii) selecting the threshold value that minimizes the calculated inaccuracy rate.

In an embodiment the reanalysis of the heart rhythm data includes (i) calculating the absolute value of the time difference between each sequential pair of intervals in the analysis segment; and (ii) comparing the maximum time difference with a threshold value to determine if the hidden regularity is present.

In an embodiment the reanalysis of the heart rhythm data includes (i) calculating the time difference between each sequential pair of intervals in the analysis segment; and (ii) comparing the maximum time difference with a threshold value to determine if the hidden regularity is present.

In an embodiment the reanalysis of the heart rhythm data includes (i) calculating the time difference between the longest interval in the analysis segment and the shortest interval in the analysis segment ("MaxDiff"); (ii) calculating the average time difference between each sequential pair of intervals in the analysis segment for which the time difference is greater than a predetermined fraction of MaxDiff; and (iii) comparing the calculated average time difference with a threshold value to determine if the hidden regularity is present.

In an embodiment the reanalysis of the heart rhythm data includes (i) calculating an average interval length for each two-interval sequence in the analysis segment ("dvals") and an average interval length for each three-interval sequence in the analysis segment ("tvals"); (ii) calculating an interval length for each two-interval sequence in the analysis segment ("dvals2") and calculating one half of the interval length for each three-interval sequence in the analysis segment ("tvals2"); (iii) calculating the difference between all unique combinations of dvals, tvals, dvals2, and tvals2 ("diffvals"); (iv) summing a predetermined number of the smallest diffvals values; and (v) comparing the summed value with a predetermined threshold to determine if the hidden regularity is present.

In an embodiment the reanalysis of the heart rhythm data includes (i) calculating the sum of the absolute difference between all pairs of intervals in the analysis segment that are separated by one interval plus the sum of the absolute difference between all pairs of intervals in the analysis segment that are separated by two intervals; (ii) summing a predetermined number of the smallest calculated sums; and (iii) comparing the sum of the predetermined number of the smallest calculated sums with a predetermined threshold to determine if the hidden regularity is present.

In an embodiment the reanalysis of the heart rhythm data includes (i) calculating the average value of the absolute value of second order differences in the analysis segment; and (ii) comparing the calculated second order difference with a predetermined threshold to determine if the hidden regularity is present.

In an embodiment, one or more of the combinatorial methods described above are applied sequentially to the analysis segment, to further improve the specificity.

A method for detecting atrial fibrillation in heart rhythm data includes monitoring the electrical activity of a heart using a wearable detector comprising an electrode, a microprocessor in signal communication with the electrodes, and a data storage component to obtain a heart rhythm data set; selecting a number of contiguous heart beat intervals as an analysis segment size; analyzing a segment of the heart rhythm data set containing the number of contiguous heart beat intervals to identify an irregularity in the segment of the heart rhythm data that is indicative of an arrhythmia, wherein the indicated arrhythmia is not necessarily AF; if an irregularity is found in the segment of the heart rhythm data, then reanalyzing the segment to identify a hidden regularity that would indicate the identified arrhythmia is not AF; and if the hidden regularity is not identified, then designating the segment of the heart rhythm data as AF and storing the segment of the heart rhythm data on the data storage component.

In another aspect of the invention, a method for determining an arrhythmia burden in heart rhythm data includes monitoring the electrical activity of a heart to obtain a heart rhythm data set; segmenting the heart rhythm data set into a plurality of segments having a predetermined number of heart beat intervals; analyzing a first segment of the heart rhythm data for a target arrhythmia using a method having high specificity; and if the method having high specificity indicates the target arrhythmia is present in the first analysis segment then (i) identifying the first segment of the heart rhythm data as indicating the target arrhythmia; (ii) analyzing or reanalyzing adjacent segments of the heart rhythm data for the target arrhythmia using a method having a higher sensitivity sequentially until the method having higher sensitivity does not indicate the target arrhythmia; and (iii) identifying an earliest segment for which the higher sensitivity method indicates the target arrhythmia as a start of the target arrhythmia and identifying a latest segment for which the higher sensitivity method indicates the target arrhythmia as an end of the target arrhythmia.

In an embodiment of the method for determining the arrhythmia burden, the higher sensitivity method comprises using different threshold values for one or more of the methods used for the high specificity method.

In an embodiment of the method for determining the arrhythmia burden, the higher sensitivity method includes using a Bayesian probability rule based on probability values that are either estimated or measured based on analyzing a database of heart rhythm data for which the arrhythmia properties of the heart rhythm data is known.

In an embodiment of the method for determining the arrhythmia burden, the higher sensitivity method includes using a hidden Markov model, with one or more of the calculated values of the high specificity and high sensitivity calculations for detecting arrhythmia as the observed output values of the model and the rhythm as the states of the model, calculating the probabilities of observing given values and the transitional probabilities by analyzing a database of heart rhythm data for which the arrhythmia properties of the heart rhythm data is known.

As is clear to one well-versed in the art, these methods and embodiments are applicable to identification and classification of other rhythm disorders other than atrial fibrillation, such as ventricular tachycardia, multifocal atrial tachycardia, and atrial flutter among others.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figures 1A, 1B, 1C:
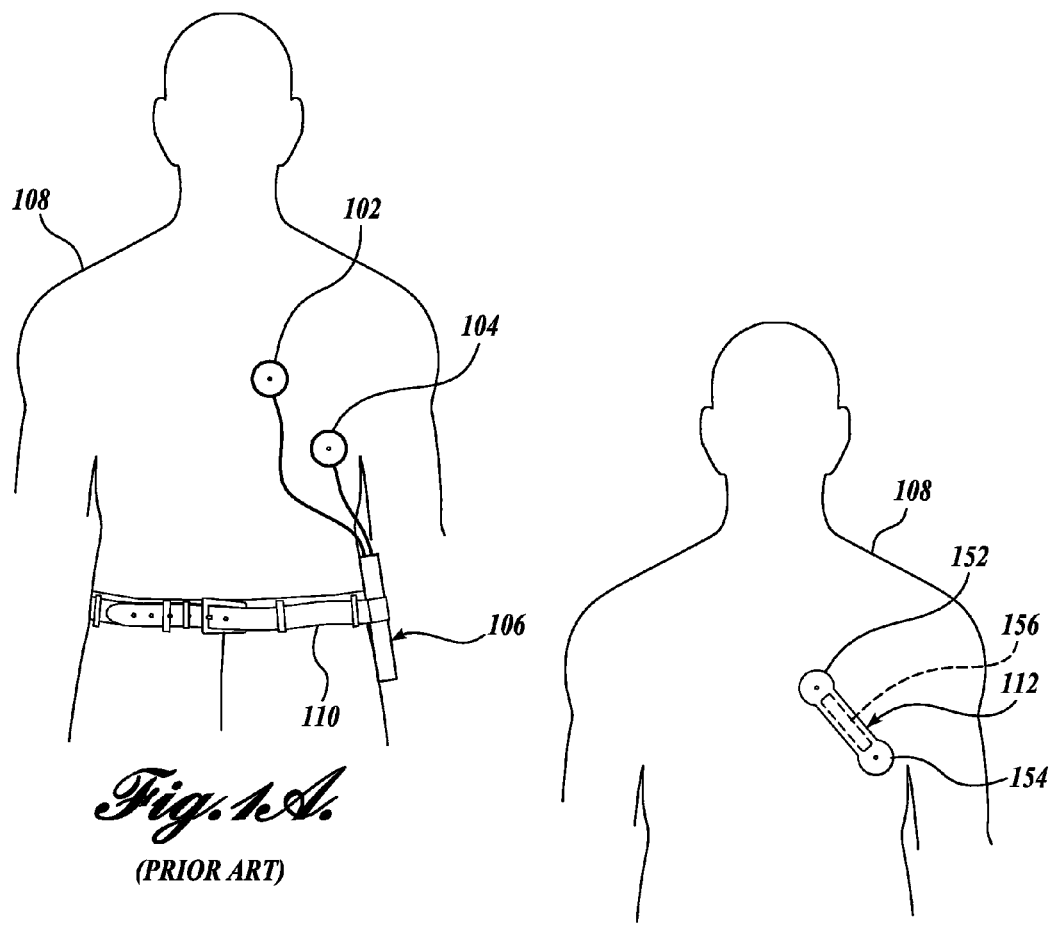
FIGS. 1A-1D illustrate prior art portable atrial fibrillation monitoring devices.

A system and a method for detecting and collecting cardiac rhythm data and/or for discriminating between classes of arrhythmia is disclosed. FIGS. 1A-1D show various illustrative portable monitoring and detection devices ("portable monitoring device"), as are known in the art. FIG. 1A shows a small, light-weight monitoring device 106 that can be used by a patient 108 daily or continuously for several months. For example, the monitoring device 106 may be carried on a belt 110 or other harness. The monitoring device 106 engages two electrodes 102, 104 that are attached directly to the patient 108 for detecting cardiac electrical activity, and having distal ends that attach to the portable monitoring device 106. The portable monitoring device 106 may be configured to continuously collect data related to cardiac activity, and stores some or all of the collected data in the internal storage component of the portable monitoring device 106.

FIG. 1B shows a portable monitoring device 112 wherein electrodes 152, 154 and a processing, data storage, and power assembly 156 is built into the body of the integrated monitoring device 112. The integrated monitoring device 112 attaches directly to the body of the patient 108 without the need for the belt 110 or other harness for supporting the device. The integrated monitoring device 112 is sufficiently thin and light-weight to securely attach to the body of the patient 108, for example, by means of adhesive surfaces, and to be worn under normal clothes without undue burden. The patient 108 may wear the integrated monitoring device 112 for extended periods of time, removing and re-attaching the integrated monitoring device 112 as necessary for other activities.

FIG. 1C illustrates an implantable monitoring device 116, which may optionally include intervention capabilities, implanted into the patient 108. For example, the device 116 may include a cardiac defibrillator that is coupled to the heart 114 through one or more leads 115 (one shown). The device 116 monitors heart rhythm to detect arrhythmia, discriminates any detected arrhythmia to identify conditions for which intervention is indicated, and administers the desired intervention. For other arrhythmias not requiring immediate intervention, the device may store the information characterizing the event for transmission or download, either immediately or at a later time.

Figure 1D:
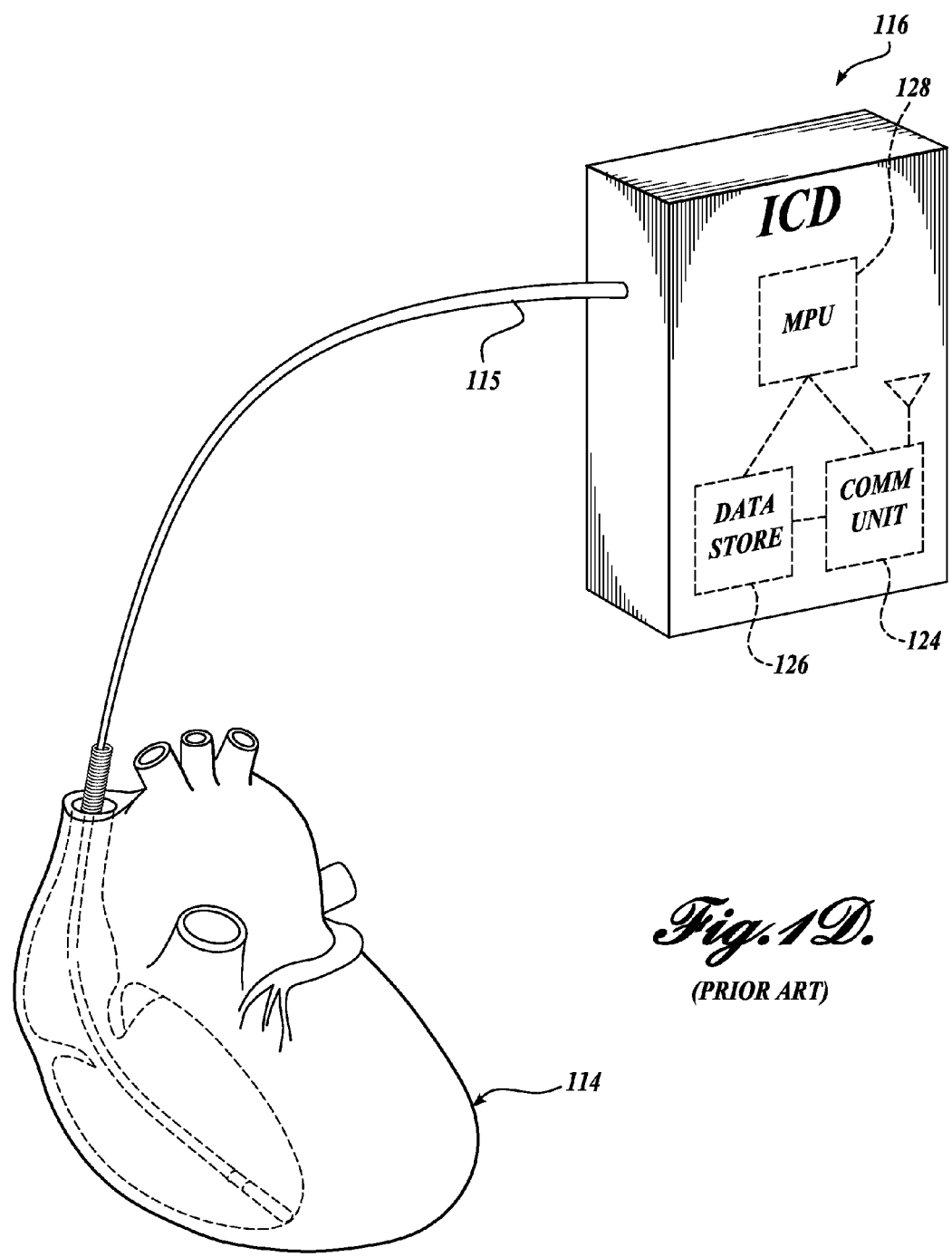

FIG. 1D shows the single-lead device 116 shown in FIG. 1C, wherein the lead is a ventricular lead 115 that extends into the patient's heart 114. Although a single-lead device 116 is shown, it will be apparent that the present invention may be implemented with a multi-lead defibrillator, e.g., a defibrillator having a coronary sinus lead, atrial lead, and ventricular lead, as are known in the art. Data collected and/or generated by the device 116 may be stored in a data store 126, which is externally readable from the device 116 via the wireless communication components 124, for further analysis. If an arrhythmia is detected, the device 116 logic component or MPU 128 determines whether a shock must be administered to treat the arrhythmia. The device 116 may include other processing components such as a microprocessor/micro-controller for executing software/firmware and controlling other functions of the device 116, a power source, such as a battery, and other hardware and/or software components known in the art and commonly used for these types of devices.

Figure 2:
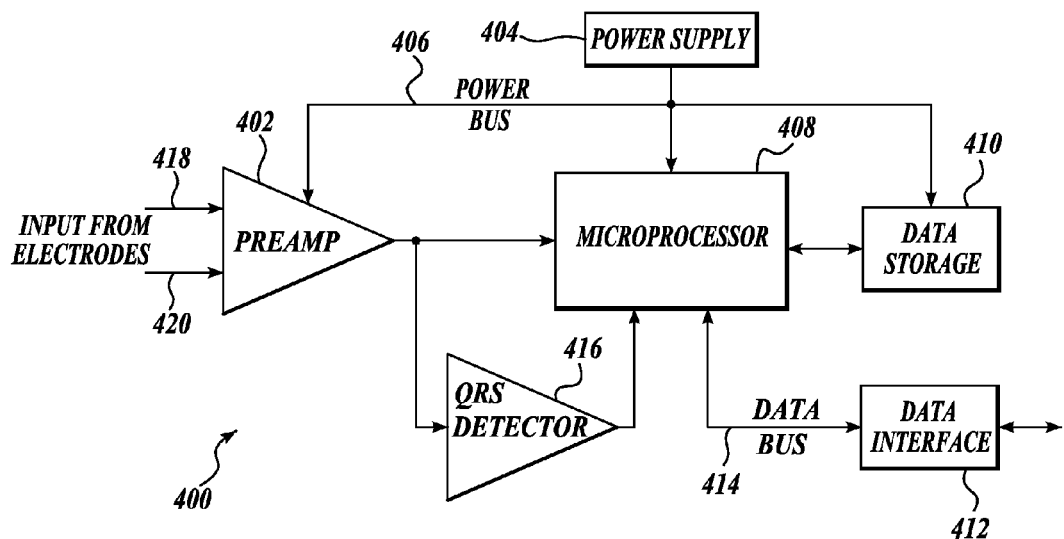
FIG. 2 is a block diagram of a prior art embodiment of a circuit for monitoring and detection of atrial fibrillation using an optional hardware-based QRS signal detector.

FIG. 2 is a block diagram showing an illustrative embodiment of a system 400 for monitoring and detection of atrial fibrillation, including an optional hardware-based QRS complex signal detector 416 ("QRS detector"). In one illustrative embodiment, the monitoring system 400 includes a preamplifier 402 for amplifying the analog electrocardiographic signals detected by electrodes and presented at input terminals 418 and 420. The output of the preamplifier 402 is input to microprocessor 408 and optional QRS detector 416. In one embodiment, the QRS detector 416 comprises a peak detector. In another embodiment, the QRS detector 416 comprises a peak detector with hysteresis. In yet another embodiment, the QRS detector 416 comprises a signal correlator that matches an input signal to a reference signal (not shown in this figure).

The microprocessor 408 is coupled with a data interface 412 via a data bus 414. The microprocessor 408 is further coupled with a data storage component 410 used for storing data collected by the microprocessor 408 from the preamplifier 402 and for storing software programs executed by the microprocessor 408. A power supply 404 supplies power to all electronic components using power bus 406. In one illustrative embodiment, the power supply 404 comprises a battery. In one illustrative embodiment, the electronic components used in the monitoring system 400 are off-the-shelf components. In another illustrative embodiment, the electronic components comprise application-specific integrated circuits or other custom-made electronics. In one embodiment, the microprocessor is a high-integration component including an analog-to-digital converter and memory and data interfaces.

The microprocessor 408 and other electronic components are selected to have low power consumption. Low power consumption of electronic components enables the monitoring system 400 to operate continuously for extended periods of time on a limited power source, such as a battery. It will be appreciated by those skilled in the art that other electronic components not shown in FIG. 2, such as LCD display, buttons, LED, and the like, may be coupled to the system 400.

The operation of the monitoring system 400 includes the pre-amplification of the analog electrocardiographic signals at input terminals 418 and 420 by the preamplifier 402. The amplified analog electrocardiographic signal at the output of preamplifier 402 is transmitted to the microprocessor 408 and QRS detector 416. The microprocessor 408 converts the analog electrocardiographic signal from the output of the preamplifier 402 to a digital electrocardiographic signal suitable for manipulation by a software program running on the microprocessor 408. In one embodiment, the software program running on the microprocessor 408 is stored in a designated section of the data storage component 410. In another embodiment, the software program running on the microprocessor 408 may be stored in a different memory component (not shown in this figure) that is distinct from the data storage component 410. Yet in another embodiment, the software program running on the microprocessor 408 may be stored in a memory component integrated with the microprocessor 408 on the same electronic chip.

The microprocessor 408 receives an output signal of the QRS detector 416 when the QRS detector 416 detects a QRS complex signal which periodically appears as a segment of the electrocardiographic signal. The software program running on the microprocessor 408 analyzes the electrocardiographic signal digitized by the microprocessor 408 and the output signal received from the QRS detector 416 and classifies the digitized electrocardiographic signal as either atrial fibrillation or other cardiac rhythms. The QRS detector 416 reduces the computational load on the microprocessor 408 by detecting the QRS complex signal and notifying the microprocessor 408 by the output signal from the QRS detector 416.

If the digitized electrocardiographic signal is classified as atrial fibrillation, then the digitized electrocardiographic signal is retained as digital electrocardiographic data in the data storage component 410. If the digitized electrocardiographic signal is classified as a cardiac rhythm other than atrial fibrillation, then the digitized electrocardiographic data in some embodiments may not be retained in the data storage component 410. Thus, in such embodiments only the digitized electrocardiographic data representing atrial fibrillation is retained in the data storage component 410, saving memory space which would otherwise be used for storing all digitized electrocardiographic data.

An alternative embodiment would store all data that is recorded, but data classified as atrial fibrillation is marked for earlier review and/or transmission to the medical facility or monitoring center.

Figure 3:
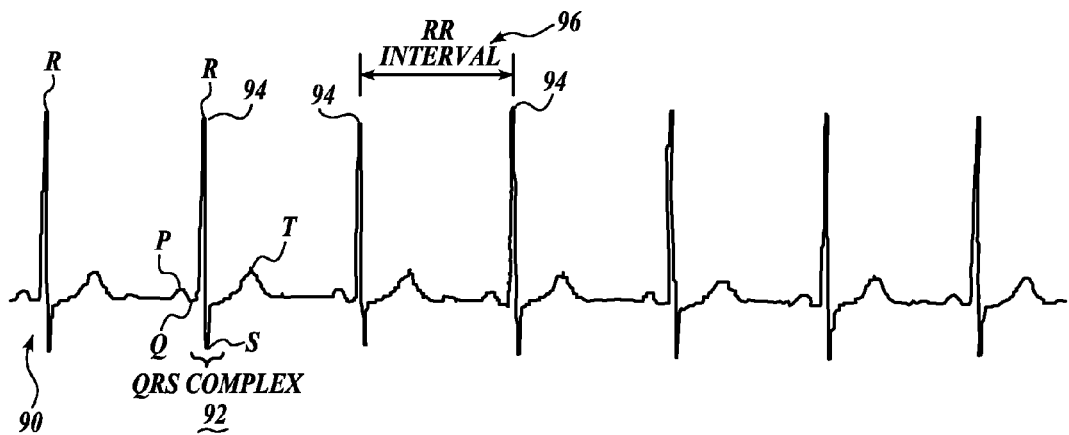
FIG. 3 is a pictorial diagram of a signal representing a heart rhythm.

FIG. 3 shows a signal 90 representing a heart rhythm, showing six complete intervals. The heart rhythm signal 90 comprises a repeating pattern of several features or waves, conventionally referred to as the P wave, Q wave, R wave, S wave and T wave. The Q, R, and S waves are referred to as the QRS complex 92. The time interval between two consecutive R waves or peaks 94 is the interbeat interval, or RR interval 96. The peak 94 is commonly used to detect a QRS complex 92.

Although systems for monitoring the electrical activity of a heart have been describes, persons of skill in the art will understand that other modes are known for monitoring the activity of the heart, including for example, pulse oximetry and phonocardiography. Such methods described herein may be applied using such other modes and methods for monitoring a heart. Currently, the most frequently used mode for monitoring a heart is to monitor the electrical activity of the heart.

When monitoring a heart rhythm over an extended period of time to detect arrhythmia, for example AF, two factors are important. First, it is important to correctly identify AF, avoiding generating a false positive. Then, when an arrhythmia is detected, it is desirable to know the duration or extent of the arrhythmia, referred to as the arrhythmia burden.

Automated methods of classification of heart rhythms analyze a contiguous portion or segment of heart rhythm data using one or more methods to generate a test value that can be used to indicate or test the regularity (or irregularity) in the analyzed segment of data. A decision rule is then applied, typically comparing the generated test value with a predetermined threshold. Based on the results of the application of the decision rule, the analyzed segment is characterized as normally rhythmic or as arrhythmic, for example, AF. The analysis may be based on the interbeat intervals, analysis of the waveform itself, or any derivative measures, including, but not limited to, mean values, differences, or standard deviations of those values. Specific methods developed by the present inventor that have been found to be particularly effective are disclosed and described in detail in U.S. Pat. Nos. 7,630,756, and 8,326,407 to Linker, both of which are hereby incorporated by reference in their entireties.

When monitoring for a particular arrhythmia (for example, AF) it is desirable to have a high degree of sensitivity in detecting the arrhythmia in subjects, but also a high specificity, to exclude subjects who do not have the disorder. If the threshold used to detect AF is stringent to substantially reduce or eliminate false positives, then only subjects that actually have AF will be identified, to a high degree of confidence. However, the stringent threshold is likely to greatly underestimate the arrhythmia burden for subjects having AF.

Figure 4:
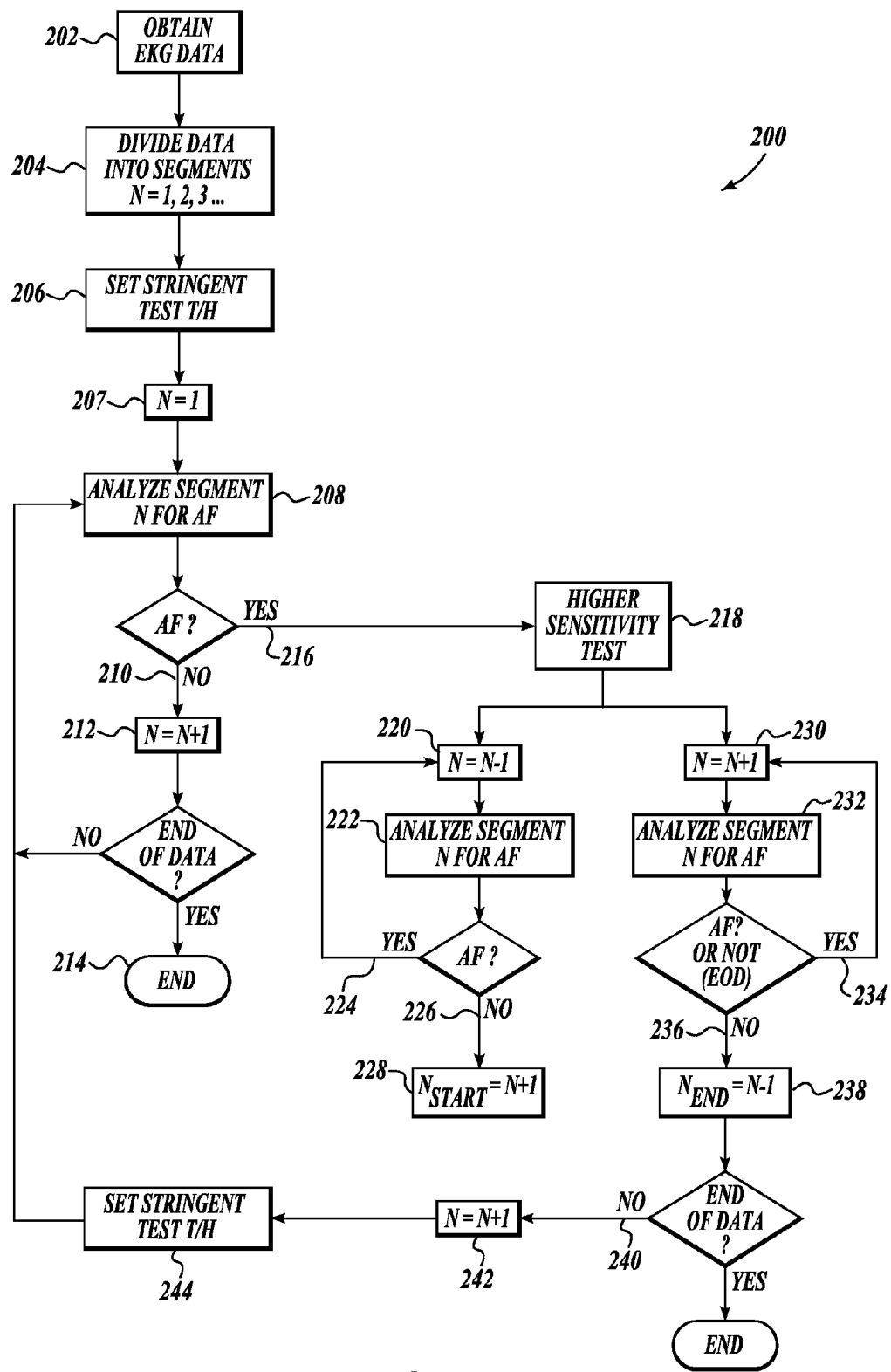
FIG. 4 is a flow chart illustrating a method for determining the extent or arrhythmic burden of a detected arrhythmia, in accordance with the present invention.

FIG. 4 illustrates a method 200 for analyzing heart rhythm data to both correctly identify episodes of AF, and to accurately estimate the duration or arrhythmia burden associated with the detected AF.

The detection method 200 includes obtaining EKG or other heart rhythm data 202 for a subject. The obtained data is divided into a plurality of segments, i.e., N segments, for analysis 204. It should be appreciated that the data need not be segmented all at one time, but may be incrementally analyzed, for example, to obtain a new segment after analyzing the preceding segment. A stringent threshold for identifying AF is set 206, such that the method is configured to identify AF with a high specificity. The first segment 207 is then analyzed using the high threshold 208. If AF is not indicated 210 in the segment, then the next segment is obtained 212, and that segment is analyzed using the high threshold 208, until all segments have been tested 214.

If a segment is found to indicate AF 216, then adjacent data is analyzed using a method having a higher sensitivity 218. For example, the threshold may be set to a relative lax value, or a completely different, higher sensitivity method may be used as discussed below. Preceding and subsequent data is analyzed for AF using the higher sensitivity method. In this example, the preceding segment of data is obtained 220 and reanalyzed for AF using the higher sensitivity method 222. For simplicity, the method will be described with reference to the hysteresis method of simply adjusting the threshold once it has been determined that AF is present.

If AF is indicated using the higher sensitivity method 224, the next preceding segment is obtained 220 and is reanalyzed for AF 222. Additional preceding segments are reanalyzed until either the first segment of the data is reanalyzed, or AF is not indicated 226, and the section or time of the first indication of AF is recorded 228. Similarly, after setting to use a higher sensitivity method 218, subsequent segments of the data are obtained 230 and analyzed for AF, for example using the more lax threshold 232. If AF is indicated in this segment 234, then the next segment of data is obtained 230 and analyzed 232 until the end of the data is reached or AF is not indicated 236, and the section or time of the end of the AF is recorded 238. If the end of the obtained data has not been reached 240, then the next segment of data is obtained 242 and analyzed for AF 208. Optionally, the test threshold may be reset to the more stringent value 244 prior to resuming analysis of the remaining data.

The fundamental idea is that once AF has been positively identified, the probability that adjacent segments of heart rhythm data are also indicative of AF is higher, even if the calculated test value is lower than the stringent threshold. Essentially, the method takes advantage of the new information that AF is present. The current method uses a simple hysteresis, applying a different test threshold to detect AF.

Other methods of modifying the test when AF has been detected may be used. For example, a Bayesian model may be used, wherein the probability of an adjacent segment being AF can be calculated based on the baseline probability of an adjacent segment being AF modified by the probability of the segment being AF given the calculated value for that segment. This method can be repeated for additional adjacent segments, and a threshold of probability determined to make the final classification. This can further be extended using a hidden Markov model, which determines the hidden states, in this case, the underlying rhythms, based on observations of the calculated values, the probability of transition between states, and expected probabilities of those values, given an underlying state.

Optionally, after the extent or arrhythmia burden of an episode of AF has been identified, the period may be further refined by applying the same methods, but beginning in the areas of data that were previously identified as not indicating AF. The method 200 may be used with any suitable analysis method for detecting arrhythmia, as discussed above, including, for example, the methods disclosed in U.S. Pat. Nos. 7,630,756, and 8,326,407 (incorporated by reference above).

A known challenge in the detection of arrhythmias from heart activity data such as EKG data is that a healthy heart may exhibit significant variability in the EKG data over time. As discussed above, prior art detection methods for detecting dangerous heart rhythm irregularities may be unsuitable for screening purposes if the method lacks sufficient specificity. When screening for arrhythmia, false positives may cause additional expense for technician review, patients may suffer unnecessary anxiety, and the false positives may result in expensive, uncomfortable, and inconvenient follow-on testing.

A heart beat rhythm may be (i) regular, (ii) regularly irregular, or (iii) irregularly irregular. An irregularly irregular rhythm exhibits no pattern to the heart beat intervals, whereas a regularly irregular rhythm exhibits an underlying or hidden pattern that may not be apparent using conventional detection methods. In particular, a healthy heart rhythm that is found to be regularly irregular is likely not to be AF. AF and other similar arrhythmias that would be useful to screen for are generally irregularly irregular.

Methods for detecting AF that rely on detecting irregularity in sequential heart beat intervals (e.g., RR intervals) to determine the likelihood that the rhythm is AF can be fooled by regular irregularity in a heart beat signal. This can lead to the automated method falsely identifying AF, i.e., a false positive. For example, a particular subject may exhibit frequent premature atrial or ventricular contractions that may lead to a false classification of AF.

Frequently, premature heart beats occur at a time shifted earlier than would be expected, but the following beat is not affected, and occurs at the time that would be expected in the absence of the premature beat. In this case, the sum of the two intervals centered on the premature beat is very close to twice the regular, "hidden" interval (it is "hidden" because neither of the two heart beat intervals are equal to this hidden interval). This pattern may be found in heart rhythms that are not a health concern, and would not indicate a potentially dangerous arrhythmia such as AF. It is also possible that more than one premature beat will occur in succession, usually in the equivalent of two or more regular, hidden intervals. In other cases an "extra" beat may occur, such that three intervals may be measured in the span of two regular, hidden intervals.

There are a number of innocuous heart beat patterns that can produce variations in measured RR intervals, but that have a hidden regularity, such that the variations in the RR intervals are not indicative of AF or other similar arrhythmia. It has been found effective to look for characteristic changes that reflect these patterns, and that can be efficiently calculated, to expose hidden regularity in otherwise irregular heart rhythm data.

If an underlying or hidden regularity in irregular heart rhythm data can be detected, the irregular heart rhythm data may be eliminated as an indicator of AF, thereby avoiding false positives and improving the specificity for detecting AF.

Figure 5:
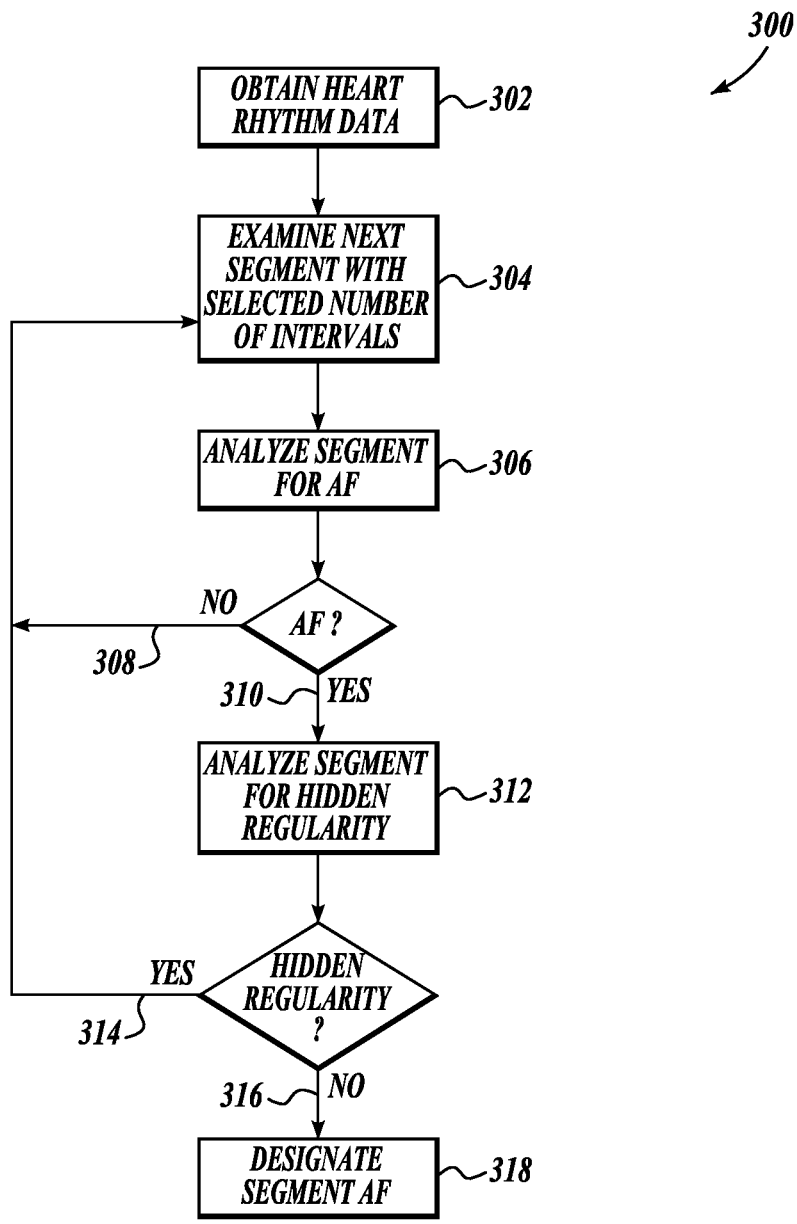
FIG. 5 is a flow chart illustrating a method for providing high specificity to a method for detecting an arrhythmia such as AF.

FIG. 5 illustrates a method 300 for providing high specificity in detecting an arrhythmia such as AF. Although for convenience FIG. 5 refers to AF, the method is readily applicable to identifying episodes of other types of unhealthy arrhythmia with high specificity. In this method 300 heart rhythm data is obtained 302 for a subject, for example EKG data. For example, the data may be obtained and analyzed in real time using a wearable monitor, such as the monitors shown in FIGS. 1A-1D, and the circuit shown in FIG. 2.

A segment of the heart rhythm data containing a predetermined number of beats or intervals is selected for analysis 304. In one exemplary embodiment, the segment is a contiguous segment of EKG data comprising more than five RR intervals. In another exemplary embodiment, the segment is a contiguous segment of EKG data comprising more than twenty intervals. In some applications, segments comprising seven intervals have been found effective. The segment is then analyzed to detect an arrhythmia 306, in this example AF. Any suitable method for detecting AF may be used, including the method disclosed in U.S. Pat. No. 8,326,407 to Linker (incorporated by reference above). If no arrhythmia is detected 308, then the next segment of data comprising the next predetermined number of heart beat intervals is selected 304, typically until all of the data has been analyzed.

If an arrhythmia is detected 310 in the analyzed segment, then the segment is analyzed for hidden regularity 312, where the hidden regularity may indicate a false positive. Particular methods for detecting hidden regularity are described below. If hidden regularity is found 314, then the segment is considered not to indicate AF, i.e., the original analysis is considered to have generated a false positive. The next data segment is then selected 304 for analysis 306 and the method continues typically until all of the data has been analyzed. If hidden regularity 316 is not found, then the data segment is designated as indicating AF, i.e., the original analysis 306 is marked AF, and considered a true positive. The next data segment may then be selected 304, and the analysis continued, typically until all of the data has been analyzed. Although the method 300 shows one step for analyzing a segment for hidden regularity, it is contemplated that more than one test may be used to detect hidden regularity, to further improve the specificity of the method.

The present inventor has developed combinatorial methods for detecting hidden regularity in heart beat rhythms, and tested the methods against standard heart rhythm data databases available from Physionet.org (i.e., afdb and CAST databases), which are well-known in the art, to find methods that were effective in screening out non-AF irregular data segments. Combinatorics is a branch of mathematics concerning the study of countable discrete structures and includes, for example, enumerative combinatorics (e.g., counting structures of a given kind), combinatorial design, external combinatorics, and combinatorial optimization (e.g., finding "optimal" objects, including largest and smallest), and algebraic combinatorics (e.g., studying combinatorial structures arising in an algebraic context, or applying algebraic techniques to combinatorial problems). The methods described below involve calculating a combinatorial property of the interval data in an analysis segment, and comparing the calculated combinatorial property with a threshold value to identify hidden regularities in the data.

MaxAdjDiff:

One effective test for detecting hidden regularity in a heart beat rhythm, referred to herein as the MaxAdjDiff method, uses the maximum absolute value of the time difference between adjacent intervals (typically measured in milliseconds) in a heart rhythm data segment, and compares this value with a predetermined threshold to determine if a hidden regularity is present.

$$\text{MaxAdjDiff} = \max\{|x_2-x_1|, |x_3-x_2|, \ldots, |x_x-x_{N-1}|\}$$

where $x_i$ is interval i (typically in msec), and N is the number of intervals in a segment of data. The calculated value MaxAdjDiff is then compared with the predetermined threshold value.

To test the potential of this method for detecting false positives, and to identify a suitable threshold, the MaxAdjDiff was calculated for publicly available database data containing annotated heart beat interval data identified as AF and heart beat interval data that is believed to be substantially non-AF. The resulting MaxAdjDiff array was then tested using a prescribed threshold rate, and the inaccuracy rate (defined below) was calculated, assuming the characteristics of the data (e.g., AF or non-AF) is known. The process was repeated a large number of times, with the prescribed threshold rate incrementally varied between the two extremes of (i) a threshold sufficiently low to characterize all of the data as AF; and (ii) a threshold sufficiently high to characterize all of the data as non-AF.

Figure 6:
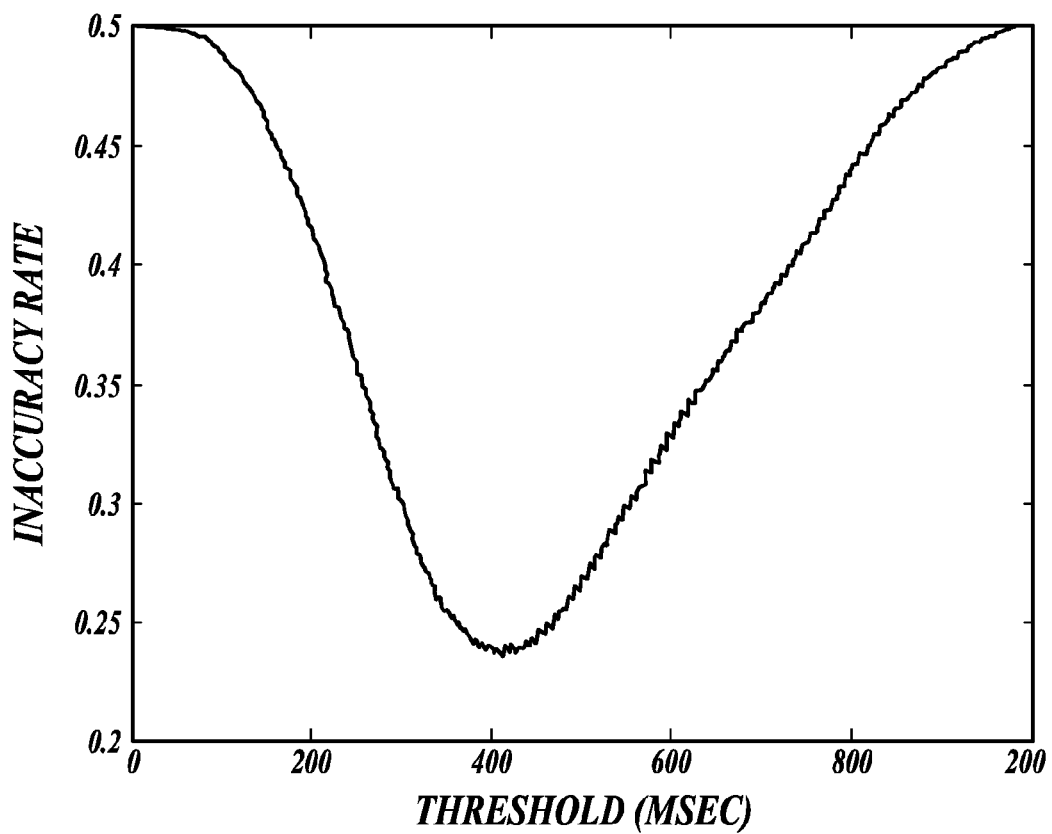
FIG. 6 is a plot showing the inaccuracy rate for the MaxAdjDiff method as a function of threshold when applied to test data having known heart rhythm characteristics.

The inaccuracy rate of each threshold was then calculated, where the inaccuracy rate is defined to be 1−Accuracy, and the Accuracy is conventionally defined as the true positive rate plus the true negative rate. The resulting curve is shown in FIG. 6, and has a minimum inaccuracy rate at a threshold value of 419 msec, wherein the inaccuracy rate was approximately 0.25. Additional details regarding the calculation of the inaccuracy rate are provided in U.S. Provisional Patent Application No. 61/642268, which is incorporated by reference above. Therefore, the maximum of the magnitude of the difference between adjacent intervals in the segment of heart rhythm data is a useful parameter for discriminating between AF and non-AF patterns.

Therefore, the MaxAdjDiff method may be applied to data obtained from monitoring a subject, e.g., using EKG data, to identify heart rhythm data that exhibits some irregularity to identify a hidden regularity in the data, and thereby avoid falsely indicating that a particular segment of data indicates AF (or other target arrhythmia).

MaxPosAdjDiff:

Another effective test for detecting hidden regularity in heart beat rhythm data is referred to herein as the MaxPosAdjDiff method. This method is similar to MaxAdjDiff, except the method looks only at the maximum positive adjacent differences in the interval data, and disregards adjacent intervals wherein the second interval in a pair is shorter than the first interval. The calculated MaxPosAdjDiff for the data segment is compared with a predetermined threshold to determine if the hidden regularity is present. This method is based on the observation that when there is ectopy, the premature beat is always early, so that the resulting RR interval is shorter. The following RR interval is typically longer. This relationship is less pronounced in AF because the RR intervals are more random. Therefore, $$\text{MaxPosAdjDiff} = \max\{x_2-x_1, x_3-x_2, \ldots, x_N-x_{N-1}\}$$

The MaxPosAdjDiff method was applied to the test database described above to calculate the inaccuracy rate. The method produced results very similar in quality to the MaxAdjDiff method, and a minimum inaccuracy rate was found, in this case at 415 msec. However, it is believed that the set of false positives identified with the MaxPosAdjDiff method will not be identical to the set of false positives obtained using the MaxAdjDiff method. Therefore, applying these two methods sequentially is expected to identify more false positives than either of the methods alone.

SumPosDiff:

Another effective method, referred to herein as SumPosDiff, calculates the average value of the positive interval changes, e.g., long interval following short interval, wherein the difference exceeds one half of the maximum possible difference in the segment being analyzed, where the maximum possible difference is the difference between the longest and shortest interval in the segment.

The calculation of SumPosDiff may be accomplished as follows:

(i) Set SumPosDiff equal to zero;
(ii) Calculate MaxDiff as the difference between the longest interval and the shortest interval in the segment;
(iii) For each interval in the segment, except the terminal interval, if the difference between the length of the interval and the length of the next succeeding interval is greater than one half of MaxDiff, add the interval to SumPosDiff;
(iv) Set SumPosDiff to the average of the intervals added to SumPosDiff; and
(v) Comparing SumPosDiff with a predetermined threshold value to determine if the hidden regularity is present.

It will be appreciated that if there are no intervals that satisfy the criteria in step (iii), then SumPosDiff will be zero. This method looks only at positive adjacent differences in the interval data that are greater than half the maximum difference in interval lengths in the segment, and takes the average of any intervals that satisfy this criteria. If SumPosDiff does not exceed a threshold value, then the segment is not indicative of AF.

The method was applied to the test database generally as described above, and a minimum inaccuracy rate was found, in this case at 391 msec.

MinCombDiff:

Another effective test for detecting hidden regularity in heart rhythm data is referred to herein as the MinCombDiff method. This method tests for hidden regular intervals in two- and three-beat interval groups. For example, if the second R wave in a segment of data occurs early, but the third R wave occurs when it otherwise would have, then $(x_2+x_1)/2$ will reflect the hidden regular interval. If both the second and the third R waves occur early, but the fourth R wave occurs at the expected time, then $(x_3+x_2+x_1)/3$ will reflect the hidden regular interval.

It is also possible that an extra beat, or R wave, will occur between two R waves that otherwise reflect the hidden regular interval, such that $(x_2+x_1)$ reflects the regular hidden interval. Another possibility is an extra beat occurs within an otherwise regular sequence of three beats, such that $(x_3+x_2+x_1)/2$ reflects the regular hidden interval. In MinCombDiff a segment of N beats is analyzed, and all of these intervals for the segment are calculated exhaustively for the segment. The calculated interval combinations are compared by taking the absolute value of the differences, which are then sorted in increasing order. The first K values from the sorted list are added, where K=N/3 represents the minimum number of matches expected. This sum will be larger for AF, and smaller if there is hidden regularity in the data.

First the intervals identified above were calculated for segments of hearth rhythm data. Using the same variable definitions as above, let, $$d\text{vals} = \{(x_1+x_2)/2, (x_2+x_3)/2, \ldots, (x_{N-1}+x_N)/2)\}$$

$$d\text{vals2} = \{(x_1+x_2), (x_2+x_3), \ldots, (x_{N-1}+x_N)\}$$

$$t\text{vals} = \{(x_1+x_2+x_3)/3, (x_2+x_3+x_4)/3, \ldots, (x_{N-2}+x_{N-1}+x_N)/3)\}$$

$$tvals2=\{(x_1+x_2+x_3)/2,(x_2+x_3+x_4)/2,\ldots,(x_{N-2}+x_{N-1}+x_N)/2)\}$$

Then we calculate the absolute value of the difference between each of these calculated intervals. Let:

$$\begin{aligned}diffvals=\{&|dvals_3-dvals_1|,\ldots,|dvals_N-dvals_1|,\\&|dvals_4-dvals_2|,\ldots,|dvals_N-dvals_2|,\ldots,\\&|dvals_N-dvals_{N-2}|,|dvals2_3-dvals2_1|,\ldots,\\&|dvals2_N-dvals2_{N-2}|,|tvals_4-tvals_1|,\ldots,\\&|tvals_N-tvals_{N-3}|,|tvals2_4-tvals2_1|,\ldots,|tvals2_N-\\&tvals2_{N-3}|,|dvals2_3-dvals_1|,\ldots,|dvals2_N-\\&dvals_{N-2}|,|dvals2_4-tvals_1|,\ldots,|dvals2_N-\\&tvals_{N-3}|,|dvals2_3-tvals2_1|,\ldots,|dvals2_N-\\&tvals2_{N-3}|,|tvals_4-dvals_1|,\ldots,|tvals_N-\\&dvals_{N-3}|,|tvals_4-tvals2_1|,\ldots,|tvals_N-\\&tvals2_{N-3}|,|tvals2_3-dvals_1|,\ldots,|tvals2_N-\\&dvals_{N-3}|\}\end{aligned}$$

This set of diffvals is then sorted in ascending order, and the first K values are summed. If the sum is less than a threshold value, then a hidden regularity is indicated, and the segment is not indicative of AF.

The MaxCombDiff method was applied to the database data, generally as discussed above, and a minimum to the inaccuracy rate was found at about 37 msec.

SumDiffPairs:

Another effective test targeting a different hidden regularity, and referred to herein as SumDiffPairs, looks at the absolute difference of RR intervals separated by one or two intervals, and adds together a number (K) of the smallest values obtained.

Let, $$IntervalDiff=\{|x_3-x_1|,|x_4-x_2|,\ldots,|x_N-x_{N-2}|,|x_4-x_1|,|x_5-x_2|,\ldots,|x_N-x_{N-3}|\}$$

The set of IntervalDiff is then sorted in ascending order and the first (smallest) K values (where K=N/3) are summed. If the sum is less than a threshold value, then the segment is not indicative of AF.

The IntervalDiff method was also applied to the database data, generally as discussed above, and a minimum to the inaccuracy rate was found at about 26 msec.

SumDiffDiff:

Another effective method, referred to herein as SumDiffDiff, targets a different hidden regularity sometimes found in hearth rhythm data. When the rhythm is a highly irregular rhythm such as bigeminy (a heart rhythm arrhythmia in which abnormal heart beats occur every other concurrent beat) or trigeminy (aberrant heart beat every third beat), the differences between adjacent RR intervals varies widely. However, the pattern is usually of no serious concern. In order to detect this hidden regularity, SumDiffDiff looks at the average value of the absolute value of second order differences in the intervals.

Let, $$SumDiffDiff = \frac{1}{N-2}\sum_{i=1}^{N-2}|(x_{i+2}-x_{i+1})-(x_{i+1}-x_i)|$$

SumDiffDiff was calculated for the database data, generally as discussed above, and a minimum to the inaccuracy rate was found at about 412 msec. If the calculated SumDiffDiff for a segment is less than the threshold rate, then the segment is not indicative of AF.

Each of the tests for hidden regularity described above identifies a different characteristic or hidden regularity in the data segment. Each of these tests can be implemented very simply and efficiently, and are not computationally difficult. It is contemplated, therefore, that two or more of these methods may be applied to a heart rhythm data set sequentially, to achieve very high confidence that a segment of data that is identified as AF is, in fact, AF.

As discussed with reference to FIG. 4 above, if an episode of the target arrhythmia is detected, it may be desirable to reanalyze other data obtained from the subject to estimate the extent or arrhythmia burden of the episode.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for detecting a target arrhythmia in heart rhythm data with high specificity, comprising:
   obtaining heart rhythm data generated by monitoring the activity of a heart with a medical monitoring device;
   selecting a predetermined number of contiguous heart beat intervals from the heart rhythm data as an analysis segment;
   analyzing the analysis segment to identify an irregularity in the heart beat intervals that satisfies a threshold test for arrhythmia;
   if an irregularity that satisfies the threshold test is identified, then reanalyzing the analysis segment to identify any hidden regularity in the heart beat intervals that would indicate absence of the target arrhythmia; and
   if the analysis segment was reanalyzed and no hidden regularity was identified, then designating the analysis segment as the target arrhythmia and storing the analysis segment and the designation on a non-transitory computer readable medium.

2. The method of claim 1, wherein the heart rhythm data comprises electrocardiograph data.

3. The method of claim 1, wherein the medical monitoring device comprises a wearable monitor.

4. The method of claim 3, wherein the wearable monitor comprises a plurality of electrodes configured to be adhesively attached to the subject, a power supply, a microprocessor configured to receive data from the plurality of electrodes, and a data storage device.

5. The method of claim 3, wherein the wearable monitor further comprises a QRS detector.

6. The method of claim 1, wherein the predetermined number of contiguous heart intervals is less than twenty-two heart beat intervals.

7. The method of claim 1, wherein the step of reanalyzing the analysis segment comprises (i) calculating a combinatorial property of the heart beat intervals in the analysis segment; and (ii) comparing the calculated combinatorial property with a threshold value to determine if the hidden regularity is present.

8. The method of claim 7, wherein the threshold value is determined by (i) analyzing a database of heart rhythm data for which the arrhythmia properties of the heart rhythm data is known; (ii) calculating an inaccuracy rate associated with comparing the calculated combinatorial property with a range of threshold values; and (iii) selecting the threshold value that minimizes the calculated inaccuracy rate.

9. The method of claim 1, wherein the step of reanalyzing the analysis segment comprises (i) calculating the absolute value of the time difference between each sequential pair of intervals in the analysis segment; and (ii) comparing the maximum time difference with a threshold value to determine if the hidden regularity is present.

10. The method of claim 1, wherein the step of reanalyzing the analysis segment comprises (i) calculating the time difference between each sequential pair of intervals in the analysis segment; and (ii) comparing the maximum time difference with a threshold value to determine if the hidden regularity is present.

11. The method of claim 1, wherein the step of reanalyzing the analysis segment comprises (i) calculating the time difference between the longest interval in the analysis segment and the shortest interval in the analysis segment ("MaxDiff"); (ii) calculating the average time difference between each sequential pair of intervals in the analysis segment for which the time difference is greater than a predetermined fraction of MaxDiff; and (iii) comparing the calculated average time difference with a threshold value to determine if the hidden regularity is present.

12. The method of claim 1, wherein the step of reanalyzing the analysis segment comprises (i) calculating an average interval length for each two-interval sequence in the analysis segment ("dvals") and an average interval length for each three-interval sequence in the analysis segment ("tvals"); (ii) calculating an interval length for each two-interval sequence in the analysis segment ("dvals2") and calculating one half of the interval length for each three-interval sequence in the analysis segment; (iii) calculating the difference between all unique combinations of dvals, tvals, dvals2, and tvals2 ("diffvals"); (iv) summing a predetermined number of the smallest diffvals values; and (v) comparing the summed value with a predetermined threshold to determine if the hidden regularity is present.

13. The method of claim 1, wherein the step of reanalyzing the analysis segment comprises (i) calculating the sum of the absolute difference between all pairs of intervals in the analysis segment that are separated by one interval plus the sum of the absolute difference between all pairs of intervals in the analysis segment that are separated by two intervals; (ii) summing a predetermined number of the smallest calculated sums; and (iii) comparing the sum of the predetermined number of the smallest calculated sums with a predetermined threshold to determine if the hidden regularity is present.

14. The method of claim 1, wherein the step of reanalyzing the analysis comprises (i) calculating the average value of the absolute value of second order differences in the analysis segment; and (ii) comparing the calculated second order difference with a predetermined threshold to determine if the hidden regularity is present.

15. The method of claim 1, wherein the step of reanalyzing the analysis segment comprises applying two or more of the steps described in claims 9-14 sequentially.

16. A method of detecting atrial fibrillation in heart rhythm data from a heart, comprising:

monitoring the electrical activity of a heart using a wearable detector comprising a plurality of electrodes, a microprocessor in signal communication with the electrodes, and a data storage component to obtain a heart rhythm data set;

selecting a segment comprising a predetermined number of contiguous heart beat intervals from the heart rhythm data set;

analyzing the segment of contiguous heart beat intervals to identify any irregularity in the segment of the heart that satisfies a threshold test for arrhythmia;

if an irregularity is identified in the segment, then reanalyzing the segment to identify any hidden regularity that would indicate the absence of atrial fibrillation; and if the segment was reanalyzed and no hidden regularity was identified, then designating the segment as atrial fibrillation and storing the segment of the heart rhythm data on the data storage component.

17. The method of claim 16, wherein the heart rhythm data set comprises electrocardiograph data.

18. The method of claim 16, wherein the step of reanalyzing the segment of the heart rhythm data comprises (i) calculating a combinatorial property of the interval data in the segment; and (ii) comparing the calculated combinatorial property with a threshold value to determine if the hidden regularity is present.

19. The method of claim 16, wherein the number of contiguous heart beat intervals in an analysis segment is not more than seven heart beat intervals.

* * * * *